(12) United States Patent
Holzapfel et al.

(10) Patent No.: US 10,405,569 B2
(45) Date of Patent: Sep. 10, 2019

(54) LANCTOBACILLUS PLANTARUM HAC01 STRAIN HAVING ANTI-INFLAMMATORY EFFICACY AND METABOLIC DISEASE ALLEVIATING EFFICACY AND USE THEREOF

(71) Applicants: ATOGEN CO., LTD., Daejeon (KR); HANDONG GLOBAL UNIVERSITY INDUSTRY-ACADEMIC COOPERATION FOUNDATION, Gyeongsangbuk-do (KR)

(72) Inventors: Wilhelm Holzapfel, Gyeongsangbuk-do (KR); Hyeunkil Shin, Gyeongsangbuk-do (KR); Chang-kee Hyun, Gyeongsangbuk-do (KR); Yosep Ji, Gyeongsangbuk-do (KR); Soyoung Park, Gyeongsangbuk-do (KR); Jihee Kang, Daejeon (KR)

(73) Assignees: ATOGEN CO., LTD., Daejeon (KR); HANDONG GLOBAL UNIVERSITY INDUSTRY-ACADEMIC COOPERATION FOUNDATION, Gyeongsangbuk-do (KR)

( * ) Notice: Subject to any disclaimer, the term of this patent is extended or adjusted under 35 U.S.C. 154(b) by 366 days.

(21) Appl. No.: 15/314,694

(22) PCT Filed: May 27, 2015

(86) PCT No.: PCT/KR2015/005296
§ 371 (c)(1),
(2) Date: May 24, 2017

(87) PCT Pub. No.: WO2016/027964
PCT Pub. Date: Feb. 25, 2016

(65) Prior Publication Data
US 2017/0251710 A1 Sep. 7, 2017

(30) Foreign Application Priority Data

Aug. 22, 2014 (KR) .................. 10-2014-0109421

(51) Int. Cl.
A01N 63/00 (2006.01)
A23L 33/135 (2016.01)
C12R 1/25 (2006.01)
C12N 1/20 (2006.01)
A23L 2/52 (2006.01)

(52) U.S. Cl.
CPC .............. *A23L 33/135* (2016.08); *A23L 2/52* (2013.01); *C12N 1/20* (2013.01); *C12R 1/25* (2013.01); *A23V 2002/00* (2013.01)

(58) Field of Classification Search
CPC ....................................... A23L 33/135
See application file for complete search history.

(56) References Cited

FOREIGN PATENT DOCUMENTS

| KR | 10-2009-0113477 A | 11/2009 |
| KR | 10-2011-0000871 A | 1/2011 |
| KR | 10-2011-0019371 A | 2/2011 |
| KR | 10-2012-0034482 A | 4/2012 |
| KR | 10-2012-0067683 A | 6/2012 |
| KR | 10-2013-0046896 A | 5/2013 |
| KR | 10-2014-0048911 A | 4/2014 |

OTHER PUBLICATIONS

Huang, Hui-Yu et al., 'Supplementation of Lactobacillus plantarum K68 and Fruit-vegetable ferment along with high fat-fructose diet attenuates metabolic syndrome in rats with insulin resistance', Evidence-Based Complementary and Alrernative Medicine, Article ID: 943020, Internal pp. 1-12, 2013, 2013.
Park, S. et al., 'The change of local and systemic immune responses triggered by Lactobacillus plantarum HSC 02 is associated with reduced visceral fat mass in a diet-induced obese mice model', Proceedings of the International Scieitific Conference on Probiotics and Prebiotics, Conference Proceedings, Jun. 24-26, 2014, pp. 44-45., 2014.
Park, Soyoung, 'Studying functional features of Lactobacillus plantarum HSC 02 from Korean white kimchi using the diet-induced obesity murine model', International Conference on Beneficial Microbes, May 27-29, 2014, p. 73, Article ID: OPB-12, 2014.

*Primary Examiner* — Albert M Navarro
(74) *Attorney, Agent, or Firm* — The PL Law Group, PLLC

(57) ABSTRACT

The present invention relates to a *Lactobacillus plantarum* HAC01 strain having anti-inflammatory efficacy and metabolic disease improving efficacy, a probiotic preparation, an anti-inflammatory composition, and a health food composition for improving a metabolic disease, which comprises, as an active ingredient, at least one selected from the group consisting of the strain, a culture product of the strain, a concentrate of the culture product, and a dried material of the culture product.

18 Claims, 5 Drawing Sheets

Specification includes a Sequence Listing.

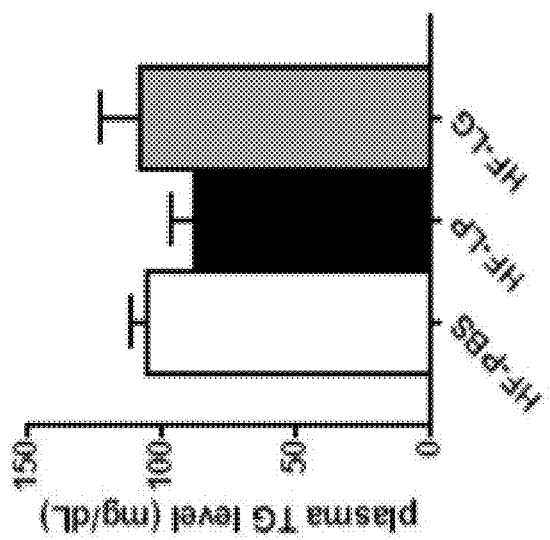
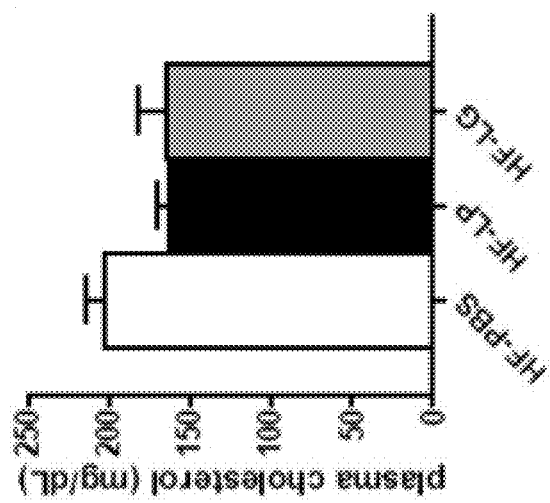
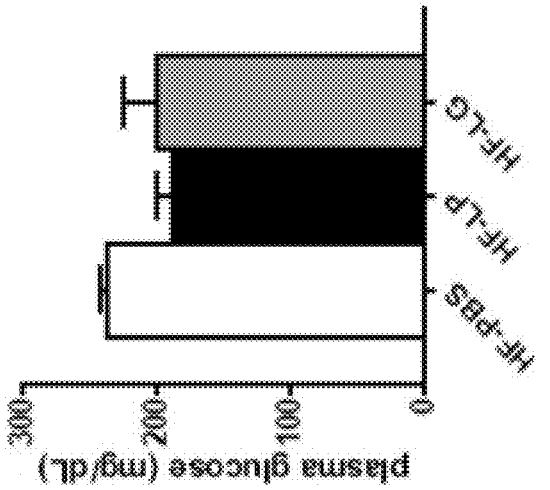

*LANCTOBACILLUS PLANTARUM* HAC01 STRAIN HAVING ANTI-INFLAMMATORY EFFICACY AND METABOLIC DISEASE ALLEVIATING EFFICACY AND USE THEREOF

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2015/005296, filed May 27, 2015, which claims priority to the benefit of Korean Patent Application No. 10-2014-0109421 filed in the Korean Intellectual Property Office on Aug. 22, 2014, the entire contents of which are incorporated herein by reference

TECHNICAL FIELD

The present invention relates to *Lactobacillus plantarum* HAC01 strain having anti-inflammatory efficacy and metabolic disease improving efficacy, and use thereof. More specifically, the present invention relates to *Lactobacillus plantarum* HAC01 strain having anti-inflammatory efficacy and metabolic disease improving efficacy, a probiotic preparation, an anti-inflammatory composition, and a health food composition for improving metabolic disease comprising, as an active ingredient, at least one selected from the group consisting of the strain, a culture product of the strain, a concentrate of the culture product and a dried material of the culture product.

BACKGROUND ART

*Lactobacillus* strains have been consumed by humans throughout history, and as a microorganism exhibiting highly beneficial effects on human health, the usefulness of this group of bacteria appears to be higher now than ever before. Thanks to extensive investigations in recent years, huge progress has been made in the understanding and application of *Lactobacillus*, and the bacteria are used in a broad application range, i.e., new drugs and health products as well as common food products are developed. Selected strains of *Lactobacillus* colonize the intestine of animals, decompose nutrients and various carbohydrates that are taken by the animals to use them as an energy source, and produce lactic acid and antimicrobial materials to protect the intestine, also by way of competition, against the growth of harmful bacteria. Accordingly, they contribute greatly to maintaining the intestinal health. In addition, *Lactobacillus* strains are widely used to promote animal growth, improve feed utilization and conversion, increase resistance to diseases, suppress growth of harmful bacteria, reduce mortality, suppress production of toxic substances, and produce various vitamins. However, to exhibit the effects as described above, the viable lactic acid bacteria must arrive in the intestine from the outside in a viable condition without any interruption. In order to exhibit their function properly in the intestine, the destruction of *Lactobacillus* by gastric acid, which is secreted following oral administration, should be minimal while strong resistance to bile acid should be exhibited.

Obesity has become a social issue for aesthetic reasons; however, the most serious problem associated with it is that it could result in serious health risks typical of metabolic disease including complications such as diabetes and hypertension. Pathological conditions related to obesity as such disease state are closely related to systemic chronic inflammation occurring in a person with obesity. The inflammatory response is an important reaction of the immune system at the local site infected by pathogenic bacteria and viruses introduced from outside. However, if the inflammatory response is chronically and systemically over-activated due to a disrupted balance in the systemic immune response, a failure in the metabolic reaction of the body is caused. Chronic inflammation caused by obesity has been known to cause various metabolic diseases such as diabetes, cardiovascular diseases, and arteriosclerosis; these are also the most important conditions for recognizing obesity as a disease. Obesity without any development of secondary metabolic diseases caused by chronic inflammation is just a simple cosmetic issue. Recently, the World Health Organization recognized obesity as a disease because obesity may be involved in chronic inflammation capable of causing a secondary metabolic disease like diabetes that can significantly reduce the quality of life.

Meanwhile, according to the Korea Patent Application Laid-Open No. 2011-0000871, "*Lactobacillus plantarum* HY7711 having anti-oxidation efficacy and anti-inflammatory efficacy and a product containing the *Lactobacillus plantarum* HY7711 as active ingredient" is disclosed. However, there is no description related to the features of the *Lactobacillus plantarum* HAC01 strain of the present invention that has both anti-inflammatory efficacy and metabolic disease improving efficacy.

SUMMARY

The present invention is devised under the circumstances described above. The inventors of the present invention isolated, from non-spicy white kimchi, *Lactobacillus plantarum* HAC01 strain that has both strong acid and bile juice resistance; also, it shows no ability to produce biogenic amines, and no transferable resistance to antibiotics. Furthermore, by confirming the inflammation improving effect and a decreased level of cholesterol, triglycerides, or the like in blood compared to the control group after a mouse is orally administered with the strain with an ultra-high fat diet, the inventors completed the present invention.

To solve the aforementioned problems, the present invention provides *Lactobacillus plantarum* HAC01 strain having both anti-inflammatory efficacy and metabolic disease improving efficacy.

The present invention further provides a probiotic preparation comprising, as an active ingredient, at least one selected from the group consisting of the strain, a culture product of the strain, a concentrate of the culture product and a dried material of the culture product.

The present invention further provides an anti-inflammatory composition comprising, as an active ingredient, at least one selected from the group consisting of the strain, a culture product of the strain, a concentrate of the culture product and a dried material of the culture product.

The present invention still further provides a health food composition for improving a metabolic disease condition, comprising, as an active ingredient, at least one selected from the group consisting of the strain, a culture product of the strain, a concentrate of the culture product and a dried material of the culture product.

*Lactobacillus plantarum* HAC01 strain of the present invention, which has excellent acid resistance and bile juice resistance but no transferable resistance to antibiotics and no ability to produce biogenic amines, and has efficacy of suppressing the expression of various inflammation-causing cytokines, is expected to be used for developing a probiotic preparation, a functional food product and food additives for alleviating chronic inflammation and also as a functional starter of a fermented food product for production of various lactic acid fermented dairy products and fermentation products. Furthermore, as the level of blood glucose, cholesterol, and triglyceride can be lowered by *Lactobacillus plantarum* HAC01 strain of the present invention, the strain can be also used for a health food product for improving a metabolic disease, and thus it is expected to have industrial applicability.

BRIEF DESCRIPTION OF THE DRAWINGS

FIGS. 1(A), 1(B), and 1(C) show the result of analyzing the level of glucose, cholesterol, and triglycerides in plasma of a mouse belonging to a group, maintained on a high-fat (HF) diet, administered with *Lactobacillus plantarum* HAC01 strain of the present invention (HF-LP), a control group (HF-PBS), or a group administered with *Lactobacillus rhamnosus* GG probiotic (HF-LG) that is used as a reference strain, in which the result is obtained by using a blood analyzer.

DETAILED DESCRIPTION

Figure 2B:
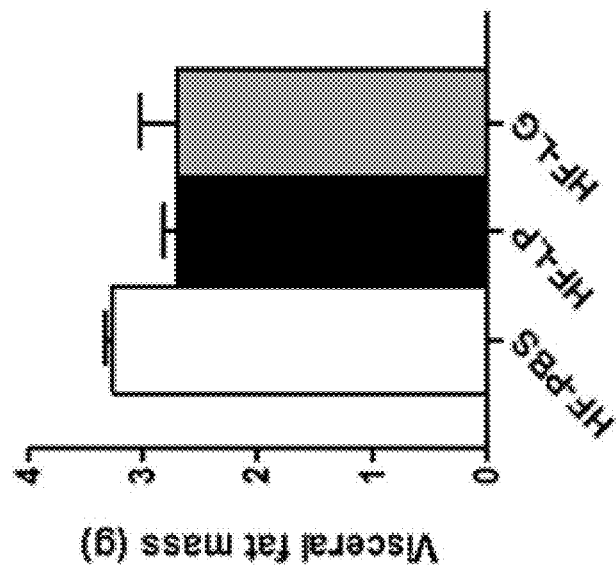
FIGS. 2(A) and 2(B) show the weight change and visceral fat mass of a mouse belonging to a group administered with *Lactobacillus plantarum* HAC01 strain of the present invention (HF-LP), a control group (HF-PBS), or a group administered with *Lactobacillus rhamnosus* GG probiotics (HF-LG) that is used as a reference strain.

In order to accomplish the purpose of the invention, the present invention provides *Lactobacillus plantarum* HAC01 strain that has anti-inflammatory efficacy and metabolic disease improving efficacy.

The inventors of the present invention isolated a lactic acid bacterial strain of *Lactobacillus plantarum* from white kimchi and, as a result of analyzing the acid resistance, bile juice resistance, resistance to antibiotics, and ability to produce biogenic amines of the isolated lactic acid bacterium, it was confirmed that the strain has excellent acid resistance and bile juice resistance but has no transferable resistance to antibiotics and no ability to produce biogenic amines. Accordingly, the isolated strain was named *Lactobacillus plantarum* HAC01 and deposited in the Korean Collection for Type Cultures (KCTC) (having the address of 181, Ipsin-gil, Jeongeup-so, Jeollabuk-do, 56212, Republic of Korea) of Korean Research Institute of Bioscience and Biotechnology having the address of 125 Gwahak-ro, Yuseong-gu, Daejeon 305-806, Republic of Korea, on Aug. 6, 2014 (accession number: KCTC 12647BP). The deposit has been made and accepted under the terms of the Budapest Treaty and all restrictions imposed by the depositor on the availability to the public of the biological material will be irrevocably removed upon the granting of a patent.

With regard to the strain of one embodiment of the present invention, the aforementioned anti-inflammatory efficacy may be exhibited by inducing an increased level of adiponectin protein which is related to alleviation of an inflammatory reaction, decreased level of leptin protein which is related to induction of an inflammatory reaction, and decreased level of mRNA expression of MCP-1 (monocyte chemo-attractant protein-1), interleukin-1b, and interleukin-12 which are related to induction of an inflammatory reaction, but the present invention is not limited to these.

Furthermore, with regard to the strain of one embodiment of the present invention, the metabolic disease improving efficacy may be by the reduction of the levels of blood glucose, cholesterol, and triglycerides. However, it is not limited to these. Metabolic disease conditions may include obesity, diabetes, hypertension, hyperlipidemia, hypercholesterolemia, arteriosclerosis, fatty liver, and other cardiovascular diseases, but not limited thereto.

The present invention further provides a probiotic preparation comprising, as an active ingredient, at least one selected from the group consisting of *Lactobacillus plantarum* HAC01 strain, a culture product of the strain, a concentrate of the culture product and a dried material of the culture product.

*Lactobacillus plantarum* HAC01 strain of the present invention has excellent acid resistance and bile juice resistance (Table 3), but it has no ability to produce biogenic amines which may induce a hypersensitive immune reaction. Further, as the strain is not observed with any resistance to antibiotics such as erythromycin, gentamycin, ampicillin, tetracycline, chloramphenicol, streptomycin, ciprofloxacin, or penicillin, it is expected to be advantageously used as a probiotic preparation.

The probiotic preparation described above can be produced and administered in various forms and by different methods that are well known in the field. For example, *Lactobacillus plantarum* HAC01 strain itself, the culture of the strain and the concentrated solution or dried product of the culture can be prepared and administered in the form of powders, liquids or solutions, tablets, capsules, syrup, suspensions or granules by mixing the strain with a carrier which is generally used for pharmaceutical purposes. Examples of the carrier include a binding agent, a lubricating agent, a disintegrating agent, a vehicle, a solubilizing agent, a dispersing agent, a stabilizing agent, a suspending agent, food colorings, and flavors, but not limited thereto. Furthermore, the dosage for administration can be adjusted properly depending on various conditions such as absorption level of the active ingredient in the body, ratio of the active ingredient in inactive form, excretion rate, the age, gender, species, condition of recipients, severeness of a disease, or the like.

The present invention further provides a food product comprising the aforementioned probiotic preparation.

The probiotic preparation of the present invention comprises, as an active ingredient, at least one selected from the group consisting of *Lactobacillus plantarum* HAC01 strain, a culture product of the strain, a concentrate of the culture product and a dried material of the culture product.

When the probiotic preparation of the present invention is used as a food additive, the probiotic preparation can be either directly added or used in combination with other food product or other food ingredients, and it can be suitably used according to a common method employed in the field. The mixing amount of the active ingredient can be suitably adjusted according to the purpose of use (e.g., for preventive or therapeutic treatment). Generally, in processes for producing a food product or a beverage, the probiotic preparation of the present invention is added in an amount of 15 parts by weight or less, and preferably 10 parts by weight or less relative to the raw materials. However, in case of long-term administration for the purpose of maintaining health and hygiene or controlling health, the mixing amount may be less than the aforementioned range. Yet, it is still possible to use the preparation in an amount that is higher than the above range because there is clearly no problem in terms of safety.

The present invention further provides an anti-inflammatory composition comprising, as an active ingredient, at least one selected from the group consisting of *Lactobacillus plantarum* HAC01 strain, a culture product of the strain, a concentrate of the culture product and a dried material of the culture product.

The anti-inflammatory composition of the present invention can increase the level of adiponectin (related to alleviation of an inflammatory reaction) protein while it can decrease the level of leptin (related to induction of an inflammatory reaction) protein in serum. By further suppressing the expression of mRNA of MCP-1, interleukin-1b, and interleukin-12, which are related to induction of an inflammatory reaction, in the spleen as a major organ to show an immunological response, the composition may exhibit the anti-inflammatory efficacy, but it is not limited thereto.

The anti-inflammatory composition of the present invention could be provided as pharmaceutical compositions or health food compositions. For the pharmaceutical composition, it may contain a carrier, a diluting agent, or a vehicle, which are pharmaceutically acceptable. For the health food composition, the health food product is not particularly limited as long as it can be administered to enhance the anti-inflammatory activity. As the health food product comprises *Lactobacillus plantarum* HAC01 strain having excellent acid resistance and bile juice resistance, it can be prepared in various forms such as lactic acid-fermented dairy products including yogurt, Calpis, cheese, and butter or other fermented food products such as tofu, fermented soy bean paste, fast-fermented soy bean paste, jelly, or kimchi, but it is not limited thereto. The mentioned fermented food and dairy products can be easily prepared according to a common method except that the bacterial strain is either substituted or amended with *Lactobacillus plantarum* HAC01 strain of the present invention.

The present invention still further provides a health food composition for improving a metabolic disease comprising, as an active ingredient, at least one selected from the group consisting of *Lactobacillus plantarum* HAC01 strain, a culture product of the strain, a concentrate of the culture product and a dried material of the culture product.

The health food composition is not particularly limited as long as it can be administered to prevent or improve a metabolic disease.

When the health food composition for improving a metabolic disease comprises, as an active ingredient, at least one selected from the group consisting of *Lactobacillus plantarum* HAC01 strain of the present invention, a culture product of the strain, a concentrate of the culture product and a dried material of the culture product is used as a food additive, the composition can be either directly added or used in combination with other food product or other food ingredients, and it can be suitably used according to a common method employed in the field. The mixing amount of the active ingredient can be suitably adjusted according to the purpose of use. Generally, in processes for producing a food product or a beverage, the composition of the present invention is added in an amount of 15 parts by weight or less, and preferably 10 parts by weight or less relative to the raw materials. However, in case of long-term administration for the purpose of maintaining health and hygiene or controlling health, the mixing amount may be less than the aforementioned range. Yet, it is still possible to use the active ingredient in an amount that is higher than the above range because there is clearly no problem in terms of safety.

Type of the food product is not particularly limited, and examples of the food product to which the health food composition of the present invention can be added include meats, sausages, breads, chocolates, candies, snacks, biscuits, pizza, ramen, noodles, gums, and dairy products including ice-cream, and all kinds of health food products in general sense are included therein.

The health beverage composition of the present invention may contain, like a common beverage, various flavors or sweetening agents, or natural carbohydrates as additional ingredients. Examples of the natural carbohydrates include monosaccharides such as glucose or fructose, disaccharides such as sucrose, polysaccharides such as dextrin or cyclodextrin, and sugar-alcohols such as xylitol, sorbitol, or erythritol. Examples of a sweetening agent which can be used include a natural sweetening agent such as thaumatin or stevia extract and a synthetic sweetening agent such as saccharine or aspartame.

Herein below, the present invention is explained in greater detail in view of the Examples. However, the following Examples are given only for specific exemplification of the present invention and by no means the scope of the present invention is limited to those examples.

EXAMPLES

Materials and Methods
Isolation and Identification of the Strain

*Lactobacillus* cells were isolated form white kimchi that has been obtained after fermentation for 10 to 15 days or more at pH of 4.5 or less. 10 g of white kimchi sample was blended with 90 mL of NaCl (0.85% NaCl/L) in a bag which has been sterilized under pressure. After homogenous mixing, 1 mL of the mixture was aliquoted and subjected to serial dilution (1:10) with 9 mL of physiological saline followed by spreading 3 times on solid MRS medium. Subsequently, it was incubated in an incubator at 37° C. for 48 hours. The cultured cells were then analyzed based on a catalase test using 0.3% hydrogen peroxide and Gram-staining method. After that, the bacterial cells with rod-shape, which are catalase negative and Gram-positive, were selected and isolated as potential candidates of the genus *Lactobacillus*.

Nucleotide sequence of the 16S rDNA of the isolated strain was analyzed to identify the species for classification. Determination of the nucleotide sequence was carried out by Solgent (South Korea).

Acid Resistance and Bile Juice Resistance Test

When a *Lactobacillus* strain is taken with foods by a person, it remains for 1 hour or so in the stomach in which strong gastric acid is secreted. Then, after staying for 2 hours or so in the duodenum in presence of bile juice at high concentration, they finally move to the "lower" intestine (jejunum and ileum). Only after the *Lactobacillus* survives under such harsh conditions and enter the intestine, they can adhere to the intestinal wall and exhibit a positive nutritional effect on the host, thus playing a role as probiotics. Accordingly, in the present invention, a test for acid resistance and bile juice resistance was carried with the *Lactobacillus* strain that has been selected by a SSDP (simulated stomach duodenum passage) method set in the conditions that are similar to those of a human body (i.e., stomach and duodenum). Simply, the isolated *Lactobacillus plantarum* strain was cultured for 18 hours in MRS broth. Then, after adding 1 mL of the culture to a sterilized disposable tube, it was centrifuged for 5 minutes at 12,000×g and 4° C. The supernatant was discarded and the cell pellet was washed twice with physiological saline. After removing the physiological saline, the precipitated cells were re-suspended and fully mixed in 10 mL of MRS broth which has been adjusted to pH 3. 1 ml of the suspension was then collected and subjected to serial dilution of 10 times followed by spreading on a solid MRS medium. Then, according to counting, CFU/mL of the initial cells was determined. The remaining 9 ml of the suspension was incubated for an hour at 37° C. and then continuously admixed well with 4 mL of bile juice (i.e., 10 g of oxgall is blended with 100 ml of distilled water and used after sterilization under pressure) and 17 mL of duodenum juice (i.e., 6.4 g $NaHCO_3$/L, 0.239 g KCl/L and 1.28 g NaCl/L are admixed well with distilled water and used after adjusting the pH to 7.4). After culture for 2 hours in an incubator at 37° C., the mixture was subjected to serial dilution of 10 times followed by spreading on a solid MRS medium, and the viable cell number was counted. Then, by comparing the CFU/mL of the initial cells, counted before, with the CFU/mL of the viable cells after 3 hours, the survival ratio was obtained.

Antibiotic Resistance Test

Each antibiotic (i.e., erythromycin, gentamycin, ampicillin, tetracycline, chloramphenicol, streptomycin, ciprofloxacin, and penicillin G) was diluted (×2) and mixed into a solid MRS medium to have a concentration of 0.025 to 64 µg/mL. *Lactobacillus plantarum* HAC01 strain that has been cultured for 18 hours was inoculated onto the solid medium with the added antibiotic so as to have a density of $10^5$/spot followed by incubation at 37° C. for 24 to 48 hours. Then, the minimal inhibitory concentration (MIC) was measured.

Biogenic Amine Production Test

Liquid MRS medium added with 0.1% of amino acid precursor tyrosine disodium salt, L-histidine monohydrochloride monohydrate, L-ornithine monohydrochloride, and L-lysine monohydrochloride was prepared. The isolated *Lactobacillus plantarum* strain was inoculated at 1% to the liquid MRS medium containing the amino acid precursor and then sub-cultured 5 to 10 times to activate the decarboxylase. The strain with activated enzyme was spread in a decarboxylase medium (i.e., 0.5% tryptone, 0.5% yeast extract, 0.5% meat extract, 0.5% sodium chloride, 0.25% glucose, 0.05% tween 80, 0.02% $MgSO_4$, 0.005% $MnSO_4$, 0.004% $FeSO_4$, 0.2% ammonium citrate, 0.001% thiamine, 0.2% $K_2PO_4$, 0.01% $CaCO_3$, 0.005% pyridoxal-5-phosphate, 1% amino acid, 0.006% bromocresol purple and 2% agar were mixed with distilled water, and used after adjusting the pH to 5.3). The cells were incubated for 24 to 48 hours at 37° C. Biogenic amine production was determined by observing the colour change into purple colour. The bromocresol purple contained in the decarboxylase medium exhibits yellow colour at pH 5.2, but it gradually turns into purple colour as the pH increases to 6.8. Thus, by taking the advantage of this change into purple colour, production of biogenic amine can be determined.

Animal Test

24 Male 7-week old C57BL/6J mice (specific pathogen free) were purchased and divided into three groups as follows (i.e., 8 animals per group). The animals were then housed in a cage for 12 hours at 23° C. and 55±10% humidity with a 12 hour light/dark cycle. As a control microorganism, commercially available *Lactobacillus rhamnosus* GG (herein below, described as LGG) was used.

A. Ultra-high fat diet (60% fat)+PBS
B. Ultra-high fat diet (60% fat)+isolated strain
C. Ultra-high fat diet (60% fat)+LGG All mice were subjected to an accommodation period of first 1 week and then, from Week 1 to Week 12 of the main test, fed with ultra-high fat diet with PBS or ultra-high fat diet mixed with the bacterial strain. Total 30 µL of PBS, or 30 µL of PBS in which the bacterial strain is diluted at a concentration of $3 \times 10^8$ cfu/day was orally administered to the animal. Water and the feed were provided ad-libitum. For total 12 weeks of the test period, the weight of the mice was measured once a week. The animals were sacrificed on the last day of the experiment by cervical dislocation, and blood, spleen and visceral fat depots were taken and weighed followed by immediate storage at −80° C. They were then used for the following tests.

Analysis of Biomarkers

The amount of blood glucose, cholesterol, and triglycerides was measured by autochemistry analyzer (Mindray BS 130, Mindray Medical, China), and the measurement was carried out at Techno-Park, Pohang, South Korea. Furthermore, the amount of adiponectin and leptin in blood was analyzed by using a mouse ELISA kit (Komabiotech, South Korea).

Total RNA was extracted from visceral fat and spleen by using mini RNeasy extraction kit (Promega, USA) according to the manufacturer's protocol, and after reverse transcription to cDNA using GoScript Reverse Transcriptase kit (Promega), the expression amount of mRNA was determined using SYBR premix EX Taq II (Takara, Japan). The analysis of the level of mRNA expression was carried out by using PCR analyzer Step one Plus (Applied Biosystems, USA) and the primers used for analysis are as described in the following Table 1.

TABLE 1

Sequence information of PCR primers

| Gene name | Forward (5'→3') (SEQ ID NO: ) | Reverse (5'→3') (SEQ ID NO: ) |
|---|---|---|
| Adiponectin | GCTCTCCTTTCCTGCCAG (1) | GAGATGCAGGTCTTCTTGGTC (2) |
| Leptin | TGACACCAAAACCCTCATA (3) | TCATTGGCTATCTGCAGCAC (4) |
| MCP-1 | CGGAACCAAATGAGATCAGAA (5) | TGTGGAAAAGGTAGTGGATGC (6) |
| IL-1b | GACCTTCCAGGATGAGGACA (7) | AGCTCATATGGGTCCGACAG (8) |
| IL-10 | TGCCTGCTCTTACTGACTGG (9) | CTGGGAAGTGGGTGCAGTTA (10) |
| TFG-β | CACTGATACGCCTGAGTG (11) | GTGAGCGCTGAATCGAAA (12) |
| Foxp3 | CCCATCCCCAGGAGTCTTG (13) | CCATGACTAGGGGCACTGTA (14) |
| IL-12 | TCACATCTCATCTCCCCAAA (15) | TCTGCTAACACATTGAGGGG (16) |
| TNF-α | ACTGCCAGAAGAGGCACTCC (17) | CGATCACCCCGAAGTTCA (18) |
| IL-6 | AGTTGCCTTCTTGGGACTGA (19) | CAGAATTGCCATTGCACAAC (20) |

Example 1

Characteristics of *Lactobacillus plantarum* HAC01 Strain

Nucleotide sequence of 16S rDNA of the rod-shaped bacterial strain isolated from white kimchi, which is catalase negative and Gram-positive, was analyzed. As a result, it was identified as *Lactobacillus plantarum* and the bacterial strain isolated in the present invention was named *Lactobacillus plantarum* HAC01.

Characteristic use of carbohydrates by *Lactobacillus plantarum* HAC01 strain, which has been isolated in the present invention, was determined according to the method described in the manual of API 50 CH kit (Biomerieux). As a result, *Lactobacillus plantarum* HAC01 strain of the present invention exhibited the characteristic use of carbohydrates as shown in the following Table 2.

TABLE 2

Characteristic use of carbohydrates by *Lactobacillus plantarum* HAC01 strain

| Type of carbohydrate | Use | Type of carbohydrate | Use |
|---|---|---|---|
| Glycerol | (+) | Esculin ferric citrate | + |
| Erythritol | − | Salicin | + |
| D-Arabinose | − | D-Celobiose | + |
| L-Arabinose | + | D-Maltose | + |
| D-Ribose | + | D-Lactose | + |
| d-Xylose | − | D-Melibiose | + |
| l-Xylose | − | D-Saccharose (sucrose) | + |
| d-Adonitol | − | D-Trehalose | + |
| Methyl-β D-xylopyranoside | − | Inulin | − |
| d-Galactose | + | D-Melezitose | + |
| d-Glucose | + | d-Raffinose | (+) |
| D-Fructose | + | Amdon (starch) | − |
| D-Mannose | + | Glycogen | − |
| L-Sorbose | − | Xylitol | − |
| L-Rhamnose | − | Gentiobiose | + |
| Dulcitol | − | D-Turanose | + |
| Inositol | − | D-Lyxose | − |
| D-Manitol | + | D-Tagatose | − |
| D-Sorbitol | + | D-Fucose | − |
| Methyl-α D-Mannopyranoside | + | L-Fucose | − |
| Methyl-α D-glucopyranoside | − | D-Arabitol | − |
| N-Acetylglucosamine | + | L-Arabitol | + |
| Amygdalin | + | Potassium 2-KetoGluconate | − |
| Arbutin | + | Potassium 5-KetoGluconate | (+) |

Example 2

Analysis of Acid Resistance and Bile Juice Resistance of *Lactobacillus plantarum* HAC01 Strain Acid resistance and bile juice resistance of *Lactobacillus plantarum* HAC01 strain that has been isolated in the present invention was analyzed. At the time of analysis, *Lactobacillus rhamnosus* GG, which is a probiotic strain well known in the field, was also tested for comparison. As a result, it was found that *Lactobacillus plantarum* HAC01 strain of the present invention exhibits higher acid resistance and higher bile juice resistance than the compared strain (Table 3).

TABLE 3

Result of analyzing acid resistance and bile juice resistance of *Lactobacillus plantarum* HAC01 strain

|  | Initial cell count (logCFU/mL) | After one hour at pH 3.0 (logCFU/mL) | After two or more hours in 3.25% oxgall (logCFU/mL) | Overall survival rate (%) |
|---|---|---|---|---|
| *Lactobacillus plantarum* HAC01 | 9.50 ± 0.029 | 9.24 ± 0.195 | 8.78 ± 0.087 | 19.38 ± 5.121 |
| *Lactobacillus rhamnosus* GG | 9.12 ± 0.311 | 8.54 ± 0.281 | 6.82 ± 0.064 | 0.54 ± 0.293 |

Example 3

Analysis of Antibiotic Resistance and Biogenic Amine Production by *Lactobacillus plantarum* HAC01

As a result of determining the antibiotic resistance of *Lactobacillus plantarum* HAC01 strain, it was found that the strain did not show, at minimum inhibitory concentration, any resistance to eight kinds of antibiotics in total, comprising erythromycin, gentamycin, ampicillin, tetracycline, chloramphenicol, streptomycin, ciprofloxacin and penicillin (Table 4).

TABLE 4

Test result for antibiotic resistance of *Lactobacillus plantarum* HAC01 strain
Unit for concentration of antibiotics: µg/ml

|  | Em | Gm | Am | Te | Ch | Sm | Ci | Pe |
|---|---|---|---|---|---|---|---|---|
| Minimum inhibitory concentration of *Lactobacillus plantarum* HAC01 (MIC) | <0.25 | 32 | 2 | 64 | 4 | >128 | 32 | 2 |
| Breakpoint for determining antibiotic resistance of *Lactobacillus plantarum* according to Danielsen & Wind | 4 | 128 | 4 | 64 | 16 | >256 | >32 | 4 |

Em: Erythromycin;
Gm: Gentamycin;
Am: Ampicillin;
Te: Tetracycline;
Ch: Chloramphenicol;
Sm: Streptomycin;
Ci: Ciprofloxacin;
Pe: Penicillin Furthermore, as a result of analyzing the ability of producing biogenic amine by *Lactobacillus plantarum* HAC01, it was found that negative response was shown for all of tyrosine, histamine, putrescin, and cadaverin, suggesting that the bacterial strain of the present invention has no ability of producing biogenic amine, which may induce a hypersensitive immune reaction (Table 5).

TABLE 5

Determination result regarding production of 4 different kinds of biogenic amines by *Lactobacillus plantarum* HAC01 strain

|  | Tyrosine | Histamine | Putrescin | Cadaverin |
|---|---|---|---|---|
| Production of biogenic amine by *Lactobacillus plantarum* HAC01 | — | — | — | — |

Example 4

Analysis of Anti-Inflammatory Effect and Effect of Improving Metabolic Disease by *Lactobacillus plantarum* HAC01 Strain

*Lactobacillus plantarum* HAC01 strain was administered to mice as a mixture with ultra-high fat diet. Then, a change in the amount of blood glucose, cholesterol, and triglycerides and a change in the expression of inflammation-related factors were determined together with the control group (ultra-high fat diet+PBS) and the comparative group (ultra-high fat diet+*Lactobacillus rhamnosus* GG).

Figure 2A:
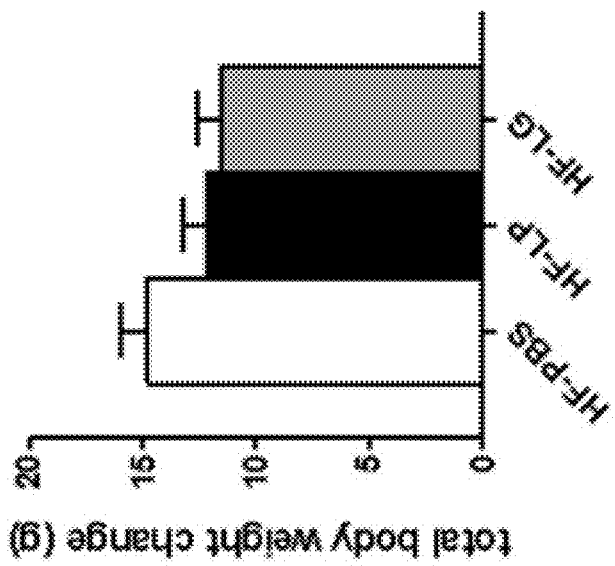

As a result, it was found that, the level of glucose and cholesterol was lower in the plasma of a mouse which has been administered with *Lactobacillus plantarum* HAC01 strain of the present invention with ultra-high fat diet compared to the control group, while it was similar to the level of the comparative group. On the other hand, the triglyceride level was found to be lower than the control group and the comparative group (FIGS. 1(A) to 1(C)). It was also found that, when compared to the control group, the weight change and visceral fat amount tend to be lower in the mouse administered with the bacterial strain of the present invention (FIGS. 2(A) and 2(B)).

Figure 3A:
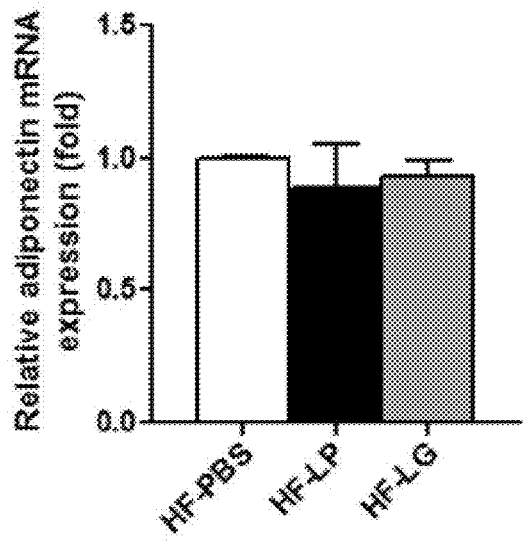
FIGS. 3(A) to 3(D) show the result of analyzing the mRNA expression amount of adiponectin which is involved with anti-inflammatory effect among the adipokines produced by intestinal adipose cells of a mouse, and leptin, MCP-1, and interleukin (IL)-1b which are involved with the occurrence of inflammation in a mouse belonging to a group administered with *Lactobacillus plantarum* HAC01 strain of the present invention (HF-LP), a control group (HF-PBS), or a group administered with *Lactobacillus rhamnosus* GG probiotics (HF-LG) used as a reference strain.
Figure 3B:
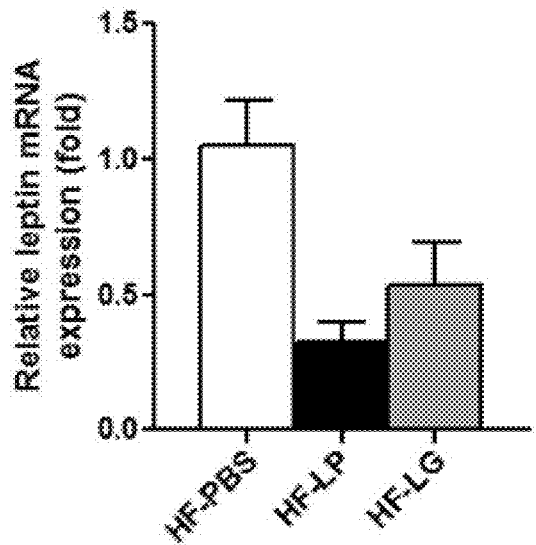
Figure 3C:
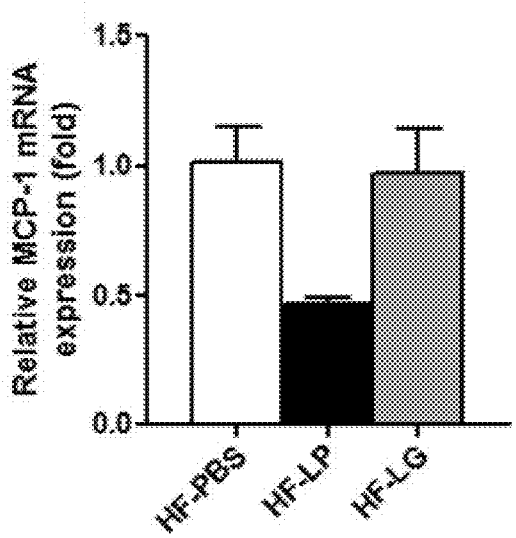
Figure 3D:
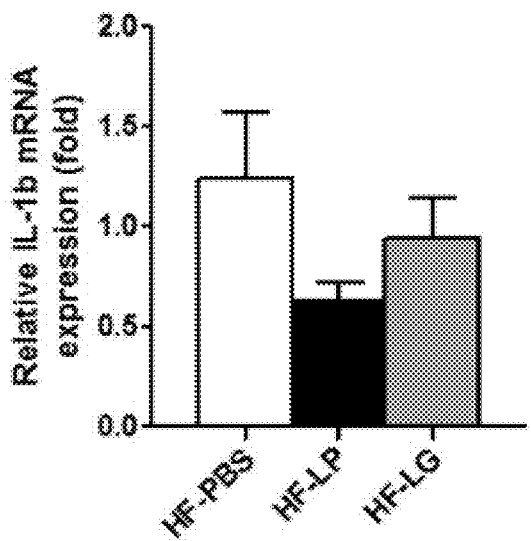
Figure 4A:
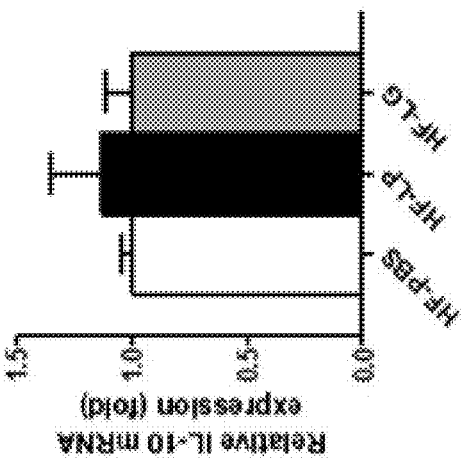
FIGS. 4(A) to 4(F) show the results of a change in the mRNA expression level of anti-inflammatory related cytokine interleukin-10, TGF-β, Foxp3 transcription factor specifically expressed in regulatory T cell, and interleukin-12, TNF-α and interleukin-6 as pro-inflammatory cytokine in the spleen of a mouse belonging to a group administered with *Lactobacillus plantarum* HAC01 strain of the present invention (HF-LP), a control group (HF-PBS), or a group administered with *Lactobacillus rhamnosus* GG probiotics (HF-LG) that is used as a reference strain.
Figure 4B:
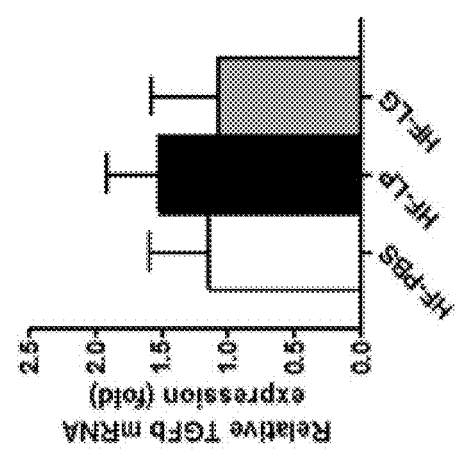
Figure 4C:
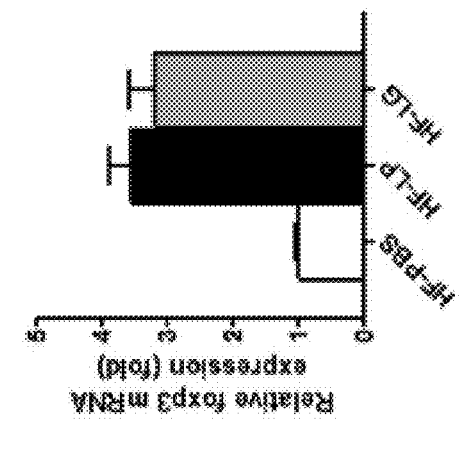
Figure 4D:
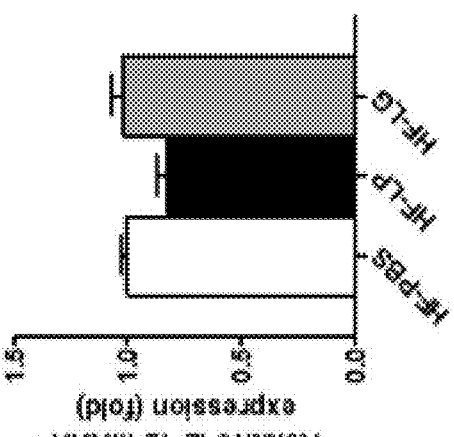
Figure 4E:
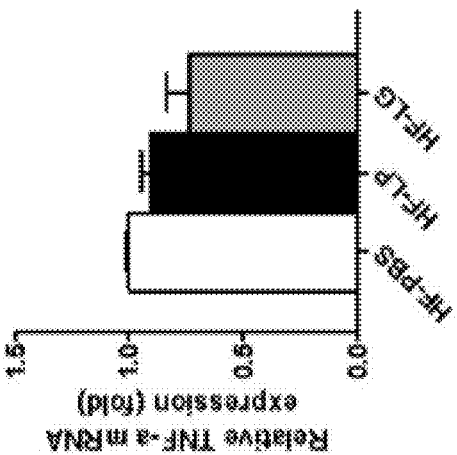
Figure 4F:
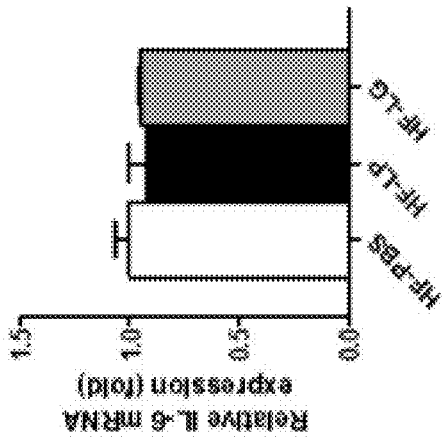
Figure 5B:
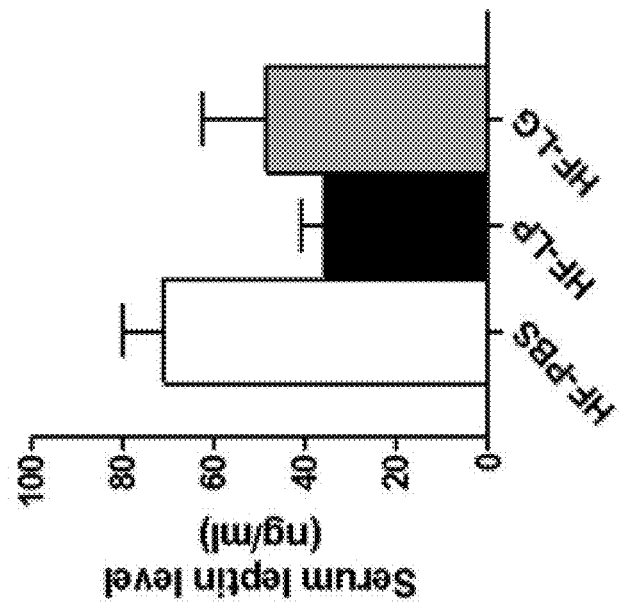
FIGS. 5(A) and 5(B) shows the change in the amount of adiponectin and leptin in the serum of a mouse belonging to a group administered with *Lactobacillus plantarum* HAC01 strain of the present invention (HF-LP), a control group (HF-PBS), or a group administered with *Lactobacillus rhamnosus* GG probiotics (HF-LG) that is used as a reference strain, in which the change amount is obtained according to measurement by ELISA.
Figure 5A:
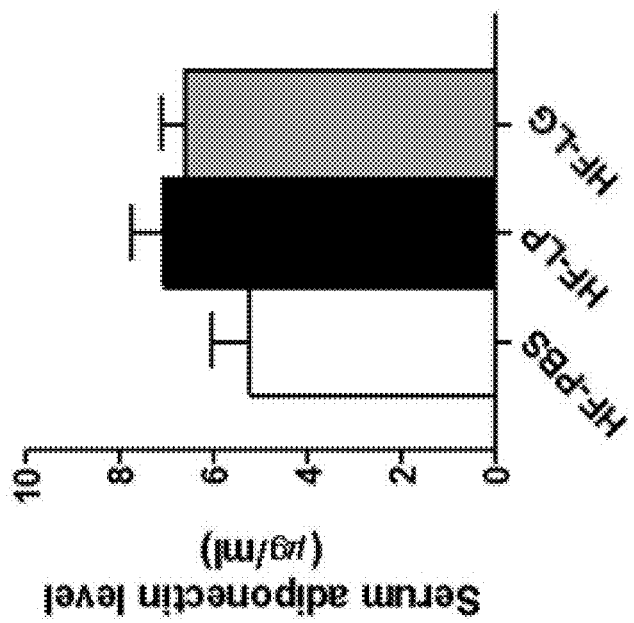

In addition, the mRNA expression level of adiponetin, which is a hormone having a property of alleviating inflammation, was found to be slightly lower in the mouse visceral fat cells when compared to the control group or the comparative group (FIG. 3(A)). The mRNA expression level of leptin, MCP-1, and interleukin-1b, which are related to induction of an inflammation, was significantly lower than the expression level in the control group and the comparative group (FIGS. 3(A) to 3(D)). Furthermore, as a result of determining the mRNA expression level of interleukin-10 and TGF-β as an anti-inflammatory cytokine in spleen, which is an important lymphoid organ showing a response to infection or inflammation, the mRNA expression level of Foxp3 as a master transcription factor related to development, maintaining, and activity of regulatory T cells, and also the mRNA expression level of interleukin-12, TNF-α, and interleukin-6 as a cytokine for inducing inflammation, it was found that the mRNA expression level of interleukin-10, TGF-β, and Foxp3 in the spleen of mice supplemented with *Lactobacillus plantarum* HAC01 strain of the present invention was higher than that of the control group and the comparative group while the mRNA expression level of an inflammation-inducing factor was the same or slightly lower than the control group or the comparative group (FIGS. 4(A) to 4(F)). Finally, the level of leptin and adiponectin as an inflammation-inducing factor in the serum of mice of each group was determined by ELISA. As a result, it was found that the amount of adiponectin protein was higher in the group administered with *Lactobacillus plantarum* HAC01 strain of the present invention than the control group or the comparative group. On the other hand, leptin was found to be lower than the control group and the comparative group (FIGS. 5(A) and 5(B)).

The invention claimed is:

1. A method for treating inflammation in a subject, the method comprising administering to the subject having the inflammation a composition comprising at least one of a *Lactobacillus plantarum* HAC01 strain deposited under the Access numbers of KCTC 12647BP, a culture product of the strain, a concentrate of the culture product, and a dried material of the culture product.

2. A method for treating a metabolic disease of a subject, the method comprising administering to the subject in need thereof a composition comprising at least one of a *Lactobacillus plantarum* HAC01 strain deposited under the Access numbers of KCTC 12647BP, a culture product of the strain, a concentrate of the culture product, and a dried material of the culture product.

3. The method of claim 1, wherein the composition is a probiotic preparation.

4. The method of claim 3, wherein the composition is a food product comprising the probiotic preparation.

5. The method of claim 1, wherein the composition comprises the *Lactobacillus plantarum* HAC01 strain.

6. The method of claim 2, wherein the composition comprises the *Lactobacillus plantarum* HAC01 strain.

7. The method of claim 1, wherein the composition comprises the culture product of the strain.

8. The method of claim 1, wherein the inflammation is chronic inflammation caused by obesity.

9. The method of claim 2, wherein the composition is a probiotic preparation.

10. The method of claim 2, wherein the metabolic disease is at least one selected from the group consisting of diabetes and hypertension.

11. The method of claim 2, wherein the metabolic disease is diabetes.

12. The method of claim 2, wherein the metabolic disease is hypertension.

13. A method for lowering a level of at least one selected from the group consisting of glucose, cholesterol, and triglycerides in blood of a subject, the method comprising administering to the subject in need thereof a composition comprising at least one of a *Lactobacillus plantarum* HAC01 strain deposited under the Access numbers of KCTC 12647BP, a culture product of the strain, a concentrate of the culture product, and a dried material of the culture product.

14. The method of claim 13, wherein the composition is a probiotic preparation.

15. The method of claim 13, wherein the level of said at least one selected from the group consisting of glucose, cholesterol, and triglycerides is the level of glucose.

16. The method claim 13, wherein the level of said at least one selected from the group consisting of glucose, cholesterol, and triglycerides is the level of cholesterol.

17. The method of claim 13, wherein the level of at least one selected from the group consisting of glucose, cholesterol, and triglycerides is the level of triglycerides.

18. The method of claim 13, wherein the composition comprises the culture product of the strain.

* * * * *

SEQUENCE LISTING

```
<160> NUMBER OF SEQ ID NOS: 20

<210> SEQ ID NO 1
<211> LENGTH: 18
<212> TYPE: DNA
<213> ORGANISM: Artificial Sequence
<220> FEATURE:
<223> OTHER INFORMATION: primer

<400> SEQUENCE: 1
gctctccttt cctgccag                                                 18

<210> SEQ ID NO 2
<211> LENGTH: 21
<212> TYPE: DNA
<213> ORGANISM: Artificial Sequence
<220> FEATURE:
<223> OTHER INFORMATION: primer

<400> SEQUENCE: 2
gagatgcagg tcttcttggt c                                             21

<210> SEQ ID NO 3
<211> LENGTH: 19
<212> TYPE: DNA
<213> ORGANISM: Artificial Sequence
<220> FEATURE:
<223> OTHER INFORMATION: primer

<400> SEQUENCE: 3
tgacaccaaa accctcata                                                19

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
tcattggcta tctgcagcac                                               20

<210> SEQ ID NO 5
<211> LENGTH: 21
<212> TYPE: DNA
<213> ORGANISM: Artificial Sequence
<220> FEATURE:
<223> OTHER INFORMATION: primer

<400> SEQUENCE: 5
cggaaccaaa tgagatcaga a                                             21

<210> SEQ ID NO 6
<211> LENGTH: 21
<212> TYPE: DNA
<213> ORGANISM: Artificial Sequence
```

```
<220> FEATURE:
<223> OTHER INFORMATION: primer

<400> SEQUENCE: 6
tgtggaaaag gtagtggatg c                                             21

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
gaccttccag gatgaggaca                                               20

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
agctcatatg ggtccgacag                                               20

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
tgcctgctct tactgactgg                                               20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
ctgggaagtg ggtgcagtta                                               20

<210> SEQ ID NO 11
<211> LENGTH: 18
<212> TYPE: DNA
<213> ORGANISM: Artificial Sequence
<220> FEATURE:
<223> OTHER INFORMATION: primer

<400> SEQUENCE: 11
cactgatacg cctgagtg                                                 18

<210> SEQ ID NO 12
<211> LENGTH: 18
<212> TYPE: DNA
<213> ORGANISM: Artificial Sequence
<220> FEATURE:
<223> OTHER INFORMATION: primer

<400> SEQUENCE: 12
gtgagcgctg aatcgaaa                                                 18
```

```
<210> SEQ ID NO 13
<211> LENGTH: 19
<212> TYPE: DNA
<213> ORGANISM: Artificial Sequence
<220> FEATURE:
<223> OTHER INFORMATION: primer

<400> SEQUENCE: 13
cccatcccca ggagtcttg                                                    19

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
ccatgactag gggcactgta                                                   20

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
tcacatctca tctccccaaa                                                   20

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
tctgctaaca cattgagggg                                                   20

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
actgccagaa gaggcactcc                                                   20

<210> SEQ ID NO 18
<211> LENGTH: 18
<212> TYPE: DNA
<213> ORGANISM: Artificial Sequence
<220> FEATURE:
<223> OTHER INFORMATION: primer

<400> SEQUENCE: 18
cgatcacccc gaagttca                                                     18

<210> SEQ ID NO 19
<211> LENGTH: 20
<212> TYPE: DNA
<213> ORGANISM: Artificial Sequence
<220> FEATURE:
<223> OTHER INFORMATION: primer
```

```
<400> SEQUENCE: 19
agttgccttc ttgggactga                                              20

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
cagaattgcc attgcacaac                                              20
```